United States Patent
Leuchs et al.

(10) Patent No.: US 11,324,788 B2
(45) Date of Patent: May 10, 2022

(54) PARVOVIRUS FORMULATION FOR TREATING TUMORS

(71) Applicants: DEUTSCHES KREBSFORSCHUNGSZENTRUM, Heidelberg (DE); RUPRECHT-KARLS-UNIVERSITÄT HEIDELBERG, Heidelberg (DE)

(72) Inventors: Barbara Leuchs, Heidelberg (DE); Karsten Geletneky, Heidelberg (DE); Jean Rommelaere, Heidelberg (DE); Christiane Dinsart, Ladenburg (DE); Michael Dahm, Munich (DE); Ottheinz Krebs, Munich (DE)

(73) Assignees: DEUTSCHES KREBSFORSCHUNGSZENTRUM, Heidelberg (DE); RUPRECHT-KARLS-UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 16/824,791

(22) Filed: Mar. 20, 2020

(65) Prior Publication Data
US 2020/0215134 A1    Jul. 9, 2020

Related U.S. Application Data

(60) Division of application No. 15/830,489, filed on Dec. 4, 2017, now Pat. No. 10,624,935, which is a (Continued)

(30) Foreign Application Priority Data

Jun. 23, 2015  (EP) ..................... 15173308

(51) Int. Cl.
A61K 39/23 (2006.01)
A61K 35/768 (2015.01)
(Continued)

(52) U.S. Cl.
CPC .......... *A61K 35/768* (2013.01); *A61K 9/0019* (2013.01); *A61K 9/0085* (2013.01);
(Continued)

(58) Field of Classification Search
None
See application file for complete search history.

(56) References Cited

U.S. PATENT DOCUMENTS

2013/0189265 A1    7/2013  Salome et al.

FOREIGN PATENT DOCUMENTS

EP    2 397 542    12/2011

OTHER PUBLICATIONS

Aucouturier et al., "Adjuvant designed for veterinary and human vaccines," Vaccine 19: 2666-2672 (Year: 2001).*

(Continued)

*Primary Examiner* — M Franco G Salvoza
(74) *Attorney, Agent, or Firm* — Duane Morris LLP; Thomas J. Kowalski; Deborah. L. Lu (57) ABSTRACT

Described is a parvovirus formulation which comprises (a) at least $1\times10^9$ pfu/ml of parvovirus H1 (H-1PV) or a related rodent parvovirus such as LuIII, Mouse minute virus (MMV), Mouse parvovirus (MPV), Rat minute virus (RMV), Rat parvovirus or Rat virus (RV) and (b) a pharmaceutically acceptable carrier containing 40-50% Iodixanol (w/v), 0.7-0.9 mmol $CaCl_2 \times 2\ H_2O$, 50-60 mmol NaCl, 0.9-1.2 mmol KCl, 0.7-0.95 mg/ml Tromethamine and 0.05-0.15 mg/ml Edetate calcium disodium. A preferred use is the therapy of a brain tumour by intratumoral injection.

17 Claims, 8 Drawing Sheets
(4 of 8 Drawing Sheet(s) Filed in Color)

Related U.S. Application Data continuation-in-part of application No. PCT/EP2016/059832, filed on May 3, 2016.

(51) Int. Cl.
| | |
|---|---|
| *A61K 9/00* | (2006.01) |
| *A61K 9/08* | (2006.01) |
| *A61K 47/24* | (2006.01) |
| *A61P 35/00* | (2006.01) |
| *A61K 47/02* | (2006.01) |
| *A61K 47/18* | (2017.01) |

(52) U.S. Cl.
CPC ............... *A61K 9/08* (2013.01); *A61K 47/02* (2013.01); *A61K 47/18* (2013.01); *A61K 47/183* (2013.01); *A61K 47/24* (2013.01); *A61P 35/00* (2018.01)

(56) References Cited

OTHER PUBLICATIONS

Palm et al., The Important of the Concentration-Temperature-Viscosity Relationship for the Development of Biologics, BioProcess International, found at https://bioprocessintl.com/manufacturing/monoclonal-antibodies/importance-concentration-temperature-viscosity-relationship-development-biologics (Year: 2015).*

Angelova et al., Tumor selectivity of oncolytic parvoviruses; from in vitro and animal models to cancer patients, Frontiers in Bioengineering and Biotechnology (2015) vol. 3, Article 55: 1-14.

Daily Med, Lactated Ringer's (sodium chloride, sodium lactate, potassium chloride and calcium chloride) Injection, retrieved as published Mar. 6, 2010 on Daily Med (http: //Dailymed.nlm.nih.gov) as demonstrated by Wayback Machine (https://web.archive.org).

GE Healthcare, New Zealand Datasheet (Apr. 30, 2012) Retrieved from http://www.medsafe.govt.nz/profs/datasheet/v/visipaqueinj.pdf.

Geletneky, et al., Bioavailability, biodistribution, and CNS toxicity of clinical-grade parvovirus H1 after intravenous and intracerebral injection in rats, Comparative Medicine (Feb. 2015) 65(1):36-45.

Geletneky, et al., Pathology, organ distribution, and immune response after single and repeated intravenous injection of rats with clinical-grade parvovirus H1, Comparative Medicine (Feb. 2015) 65 (1 ):23-35.

Geletneky, et al., Phase I/IIa study of intratumoral/intracerebral or intravenous/intracerebral administration of Parvovirus H-1 (ParvOryx) in patients with progressive primary or recurrent glioblastoma multiforme: Parv0ryx01 protocol, BMC Cancer (Mar. 2012) 12(99):1-9.

Marchini, et al., Oncolytic parvoviruses: from basic virology to clinical applications, Virology Journal (Feb. 2015) 12(6).

International Search Report and Written Opinion dated Jul. 5, 2016, issued in Application No. PCT/EP2016/059832.

IPRP dated Sep. 5, 2017, issued in Application No. PCT/EP2016/059832.

* cited by examiner

PARVOVIRUS FORMULATION FOR TREATING TUMORS

RELATED APPLICATIONS AND INCORPORATION BY REFERENCE

This application is a divisional of U.S. application Ser. No. 15/830,489 filed Dec. 4, 2017, which is a continuation-in-part application of international patent application Serial No. PCT/EP2016/059832 filed May 3, 2016, which published as PCT Publication No. WO 2016/206844 on Dec. 29, 2016, which claims benefit of European patent application Serial No. 15173308.6 filed Jun. 23, 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a parvovirus formulation where the parvovirus is present in a concentration of at least $1\times10^9$ pfu/ml in a pharmaceutically acceptable carrier containing 40-50% Iodixanol (w/v), 0.7-0.9 mmol $CaCl_2 \times 2$ $H_2O$, 50-60 mmol NaCl, 0.9-1.2 mmol KCl, 0.7-0.95 mg/ml Tromethamine and 0.05-0.15 mg/ml Edetate calcium disodium. The carrier has a viscosity between 3 to 5 mPa·s at 37° C. to 40° C.

BACKGROUND OF THE INVENTION

Cancer is the second leading cause of death worldwide. It has been estimated that half of men and one third of women will be diagnosed with some form of cancer during their lifespan. Moreover, because cancer is predominantly a disease of aging, the number of cancer deaths worldwide is predicted to increase about 45% from 2007 to 2030 (from 7.9 million to 11.5 million deaths) due to the increase proportion of elderly people (WHO estimates, 2008). Cancer is also the most costly disease. The latest estimates from the National Cancer Institute showed that the overall economic cost of cancer in the U.S. in 2007 was $226.8 billion and unless more successful preventive interventions, early detection and more efficient treatments will be developed, this already huge economic burden is expected to further grow during the next two decades. Despite significant progresses in the prevention, detection, diagnosis and treatment of many forms of cancer, which is testified by an increase of the percentage of 5-years cancer survivals in U.S. and in Europe over the last thirty years, some tumour types, such as pancreatic, liver, lung, brain remain orphan of effective treatments calling for the development of new therapeutic options. Oncolytic viruses, which exploit cancer-specific vulnerabilities to kill cancer cells while sparing normal cells are fast emerging as promising tools for fighting cancer. No less than twelve different oncolytic viruses are currently undergoing phase I-III clinical trials against various malignancies used alone or in combination with other anticancer agents. Among them, the oncolytic rat parvovirus H-1PV is currently evaluated for safety and first signs of efficacy in a phase I/IIa clinical trial in patients having recurrent glioblastoma multiforme (GBM) (Geletneky et al, BMC Cancer 2012, pp. 99).

H-1PV is a small (~25 nm in diameter), non-enveloped icosahedral particle containing a 5.1 kb long single-stranded DNA genome. The genomic organization of H-1PV consists of two transcriptional units under the control of two promoters, the P4 early promoter and P38 late promoter. P4 regulates the expression of the gene encoding the non-structural (NS) proteins (NS1 and NS2) and the P38 the one encoding the capsid (VP) proteins (VP1, VP2, VP3). The virus multiplies preferentially in fast dividing cancer cells. This onco-selectivity is not based on a better uptake of the virus by cancerous cells, but rather is due to the fact that cancer cells overexpress factors, such as cyclin A, E2F, or CREB/ATF, required for virus DNA replication. Cancer therapy using a parvovirus and its combination with chemotherapy or an HDAC inhibitor has been recently described (WO 2009/083232 A1; WO 2011/113600 A1).

One frequent problem of local therapy of tumors by injection or infusion of oncolytic viruses is the targeted distribution of the inoculum and a loss of active substance. In particular, when a catheter is used the distribution takes place along the catheter track due to an area of diminished resistance along the path of the catheter through the tissue. This phenomenon is also known as backflow.

Citation or identification of any document in this application is not an admission that such document is available as prior art to the present invention.

SUMMARY OF THE INVENTION

Therefore, it is the object of the present invention to provide a pharmaceutical composition which does not suffer under the problem of backflow upon administration and is stable during a storage time of at least 12 months, even under elevated temperature conditions for several days and UV treatment.

According to the invention this is achieved by the subject matters defined in the claims.

Thus, the present invention provides a pharmaceutical composition which may comprise (a) a parvovirus H1 (H-1PV) or a related rodent parvovirus selected from the group consisting of LuIII, Mouse minute virus (MMV), Mouse parvovirus (MPV), Rat minute virus (RMV), Rat parvovirus or Rat virus (RV) in a concentration of at least $1\times10^9$ pfu/ml and (b) a pharmaceutically acceptable carrier containing 40-50% Iodixanol (w/v), 0.7-0.9 mmol $CaCl_2 \times 2$ $H_2O$, 50-60 mmol NaCl, 0.9-1.2 mmol KCl, 0.7-0.95 mg/ml Tromethamine and 0.05-0.15 mg/ml Edetate calcium disodium. The pharmaceutical acceptable carrier has a viscosity between 3 and 5 mPa·s at 37 to 40° C.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

Thus, the present invention provides a pharmaceutical composition which may comprise (a) a parvovirus H1 (H-1PV) or a related rodent parvovirus selected from the group consisting of LuIII, Mouse minute virus (MMV), Mouse parvovirus (MPV), Rat minute virus (RMV), Rat parvovirus or Rat virus (RV) in a concentration of at least $1 \times 10^9$ pfu/ml and (b) a pharmaceutically acceptable carrier having a viscosity between 3 and 5 mPa·s at 37 to 40° C. and containing 40-50% Iodixanol (w/v), 0.7-0.9 mmol $CaCl_2 \times 2$ $H_2O$, 50-60 mmol NaCl, 0.9-1.2 mmol KCl, 0.7-0.95 mg/ml Tromethamine and 0.05-0.15 mg/ml Edetate calcium disodium.

DETAILED DESCRIPTION OF THE INVENTION

The term "parvovirus" as used herein may comprise wild-type or modified replication-competent derivatives thereof. Suitable modified parvoviruses which can be used for actively producing said parvoviruses and which are useful for therapy, are readily determinable within the skill of the art based on the disclosure herein, without undue empirical effort.

According to the present invention, the parvovirus of the composition includes parvovirus H1 (H1PV) or a related parvovirus such as LuIII, Mouse minute virus (MMV), Mouse parvovirus (MPV), Rat minute virus (RMV), Rat parvovirus (RPV) or Rat virus (RV).

According to the invention the parvovirus is present in an effective dose in a concentration of or higher than $1 \times 10^9$ pfu/ml and combined with a pharmaceutically acceptable carrier containing 40-50% Iodixanol (w/v), 0.7-0.9 mmol $CaCl_2 \times 2$ $H_2O$, 50-60 mmol NaCl, 0.9-1.2 mmol KCl, 0.7-0.95 mg/ml Tromethamine and 0.05-0.15 mg/ml Edetate calcium disodium. In particular, the carrier contains 45-49% Iodixanol (w/v), 0.75-0.85 mmol $CaCl_2 \times 2$ $H_2O$, 50-55 mmol NaCl, 0.95-1.1 mmol KCl, 0.8-0.9 mg/ml Tromethamine and 0.05-0.10 mg/ml Edetate calcium disodium. In a most preferred embodiment the carrier contains 48% Iodixanol (w/v), 0.81 mmol $CaCl_2 \times 2$ $H_2O$, 52.80 mmol NaCl, 1.06 mmol KCl, 0.88 mg/ml Tromethamine and 0.07 mg/ml Edetate calcium disodium.

"Pharmaceutically acceptable" is meant to encompass any carrier, which does not interfere with the effectiveness of the biological activity of the active ingredients and that is not toxic to the patient to whom it is administered. In addition, to the above defined carrier composition, the pharmaceutical formulation according to the present invention may contain additional pharmaceutical carriers. Examples of suitable additional pharmaceutical carriers are well known in the art and include mannitol, sorbitol, glucose or sucrose. Such carriers can be formulated by conventional methods.

An "effective dose" refers to amounts of the active ingredients that are sufficient to affect the course and the severity of the disease, leading to the reduction or remission of such pathology. An "effective dose" useful for treating and/or preventing these diseases or disorders may be determined using methods known to one skilled in the art. In addition, to ensure storage stability of the formulation, the active ingredient, i.e. the parvovirus, should be present in a concentration of at least $1 \times 10^9$ pfu/ml, particularly at least $5 \times 10^9$ pfu/ml, $1 \times 10^{10}$ pfu/ml or $1 \times 10^{11}$ pfu/ml. In a preferred embodiment the concentration is between $1 \times 10^9$ pfu/ml and $1 \times 10^{10}$ pfu/ml, in particular 1×, 2×, 3×, 4×, 5×, 6×, 7×, 8× or $9 \times 10^9$ pfu/ml. In another preferred embodiment the the concentration is between $1 \times 10^{10}$ pfu/ml and $1 \times 10^{11}$ pfu/ml, in particular 1×, 2×, 3×, 4×, 5×, 6×, 7×, 8× or $9 \times 10^{10}$ pfu/ml.

According to the present invention, the viscosity of the carrier is between 3.5 to 4.5 mPa·s at 37 to 40° C. More preferred is a carrier wherein the viscosity of the carrier is between 4 and 5 mPa·s. Even more preferred is a carrier having a viscosity of about 4.5 mPa·s. This viscosity resembles the viscosity of blood (Rosenson et al., Clinical Chemistry, 42:8, pp. 1189-1195 (1996).

According to a preferred embodiment of the present invention, the carrier is iodixanol in Ringer solution that is prepared by mixing, 73.62% VISIPAQUE™ (iodixanol) 320 (GE Healthcare) with 26.38% Ringer solution. VISIPAQUE™ (iodixanol) 320 (GE Healthcare) contains 652 mg/ml Iodixanol (=65.2% iodixanol) so that the iodixanol concentration after mixing with Ringer solution is 48%. "Iodixanol" is a synonym for "VISIPAQUE™" (for human injection use) or "Iodixanolum" (research grade). The chemical structure is EINKLEBEN.

The IUPAC name is 5-[acetyl-[3-[N-acetyl-3,5-bis(2,3-dihydroxypropylcarbamoyl)2,4,6,-triiodoanilino]2-hydroxypropyl]amino]-1-N,3,N-bis(2,3-dihydroxypropyl)-2,4,6-triiodobenzene-1,3-dicarboxamide. The CAS number is 92339-11-2. It is also a well known contrast agent for CT imaging.

Administration may be effected by different ways, e.g. by intravenous, intraperitoneal, subcutaneous, intramuscular, intradermal or intratumoral administration. The route of administration, of course, depends on the kind of therapy and the kind of compounds contained in the pharmaceutical composition. A preferred route of administration is intratumoral or intravenous administration. The dosage regimen is readily determinable within the skill of the art, by the attending physician based on patient data, observations and other clinical factors, including for example the patient's size, body surface area, age, sex, the particular parvovirus, cell etc. to be administered, the time and route of administration, the tumor type and characteristics, general health of the patient, and other drug therapies to which the patient is being subjected.

The pharmaceutical composition of the present invention is useful for the treatment of any tumor type, in particular (but not exclusively) brain tumor (e.g. glioma and glioblastoma), pancreatic carcinoma, cervical carcinoma, lung cancer, head and neck cancer, breast cancer or colon cancer.

Patients treatable by the pharmaceutical composition according to the invention include humans as well as non-human animals. Examples of the latter include, without limitation, animals such as cows, sheep, pigs, horses, dogs, and cats.

From the clinical data as shown in Example 1 it can be concluded that the use of VISIPAQUE™ (iodixanol) 48% allows for (i) precise visualization of the inoculum by CT, (ii) precise local delivery as a result of the higher viscosity and (iii) the absence of backflow even when manual injection and no prolonged and automated injection such as convection enhanced delivery (CED) was used. This favorable pattern of distribution is most likely due to the different physical properties of VISIPAQUE™ (iodixanol) 48% compared with watery solutions. VISIPAQUE™ (iodixanol) 48% in Ringer solution with a refraction index of 1.41 has a viscosity at 37° C. of 4 mPa·s, water at 37° C. of ~0.7 mPa·s. The human blood at 37° C. has a viscosity of 3-5 mPa·s. Therefore, the injection formulation is close to blood that means in a physiological value of blood.

Figure 5:
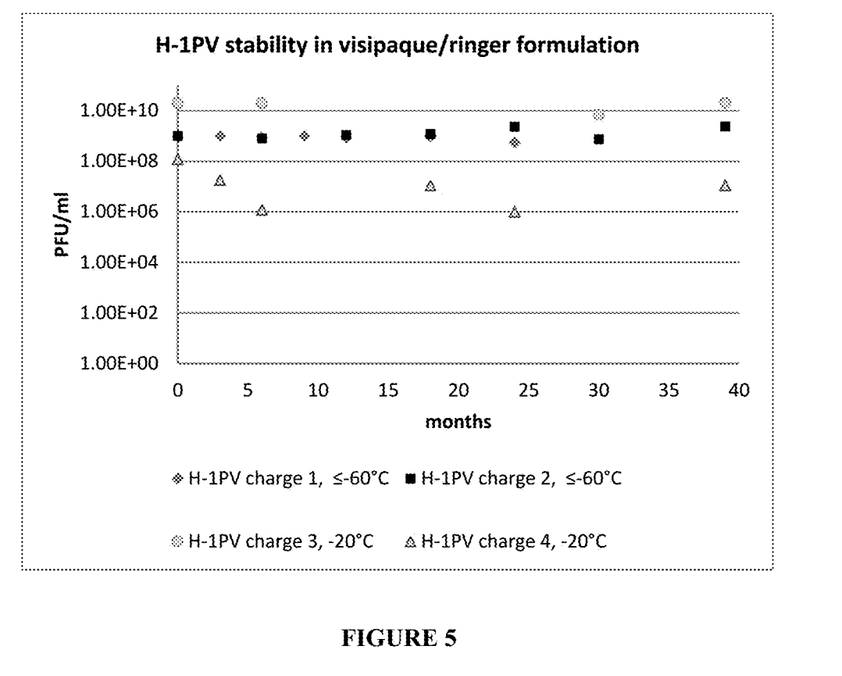
FIG. 5: Virus Concentration in Iodixanol/Ringer solution [73.62% VISIPAQUE™ (iodixanol) 320(GE Healthcare) mixed with 26.38% Ringer solution].

The inventors have found out that the virus concentration has an influence on the stability of the formulation (FIG. 5). To ensure a storage stability of at least 12 months the virus concentration should be at least $1 \times 10^9$ pfu/ml in a 48% Iodixanol/Ringer solution that has been obtained by mixing 73.62% (w/v) VISIPAQUE™ (iodixanol) 320 (GE Healthcare) with 26.30% (w/v) Ringer solution. The obtained solution contains 48% Iodixanol (w/v), 0.81 mmol $CaCl_2 \times 2 H_2O$, 52.80 mmol NaCl, 1.06 mmol KCl, 0.88 mg/ml Tromethamine and 0.07 mg/ml Edetate calcium disodium.

In a preferred embodiment the storage stability is at least 18 months, at least 24 months, at least 30 months, at least 36 months or even up to 48 months.

Figure 6:
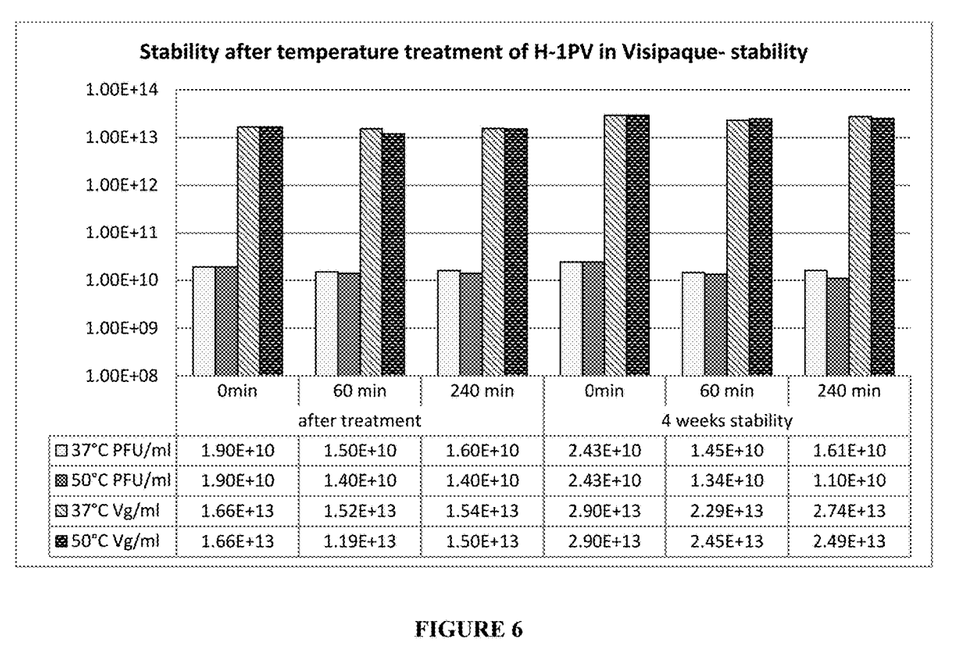
FIG. 6: Treatment of H-1 PV in Iodixanol/Ringer solution at elevated temperature.
Figure 7A:
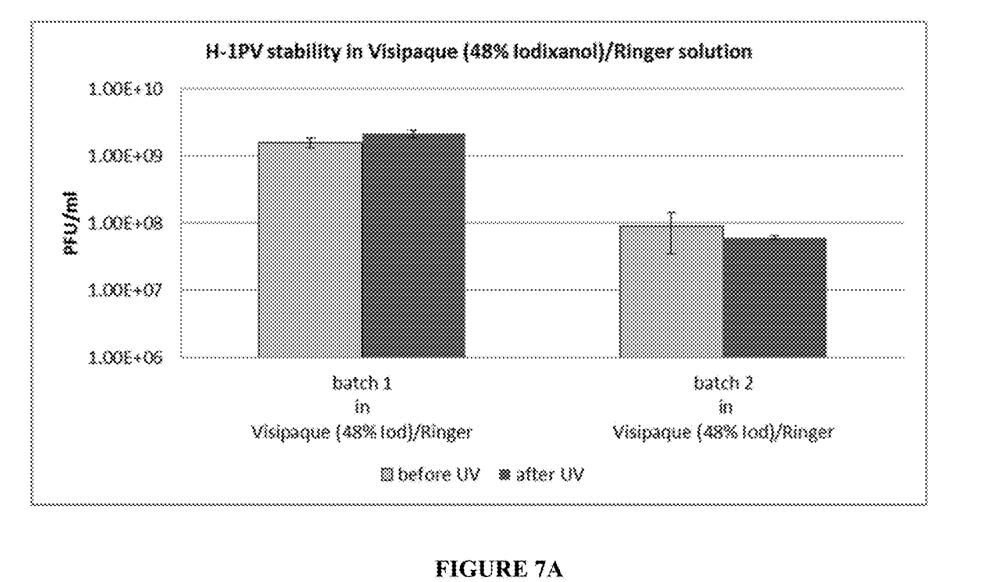
FIGS. 7A-7C: UV-Treatment of H-1 PV in two Iodixanol/Ringer solutions (A,B) and Tris-EDTA buffer (C).
Figure 7B:
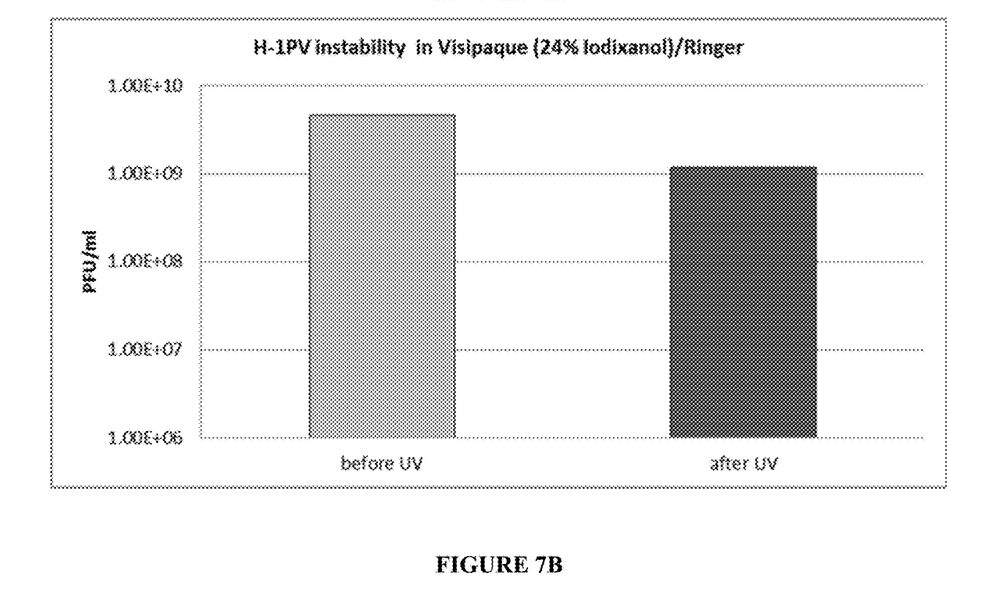
Figure 7C:
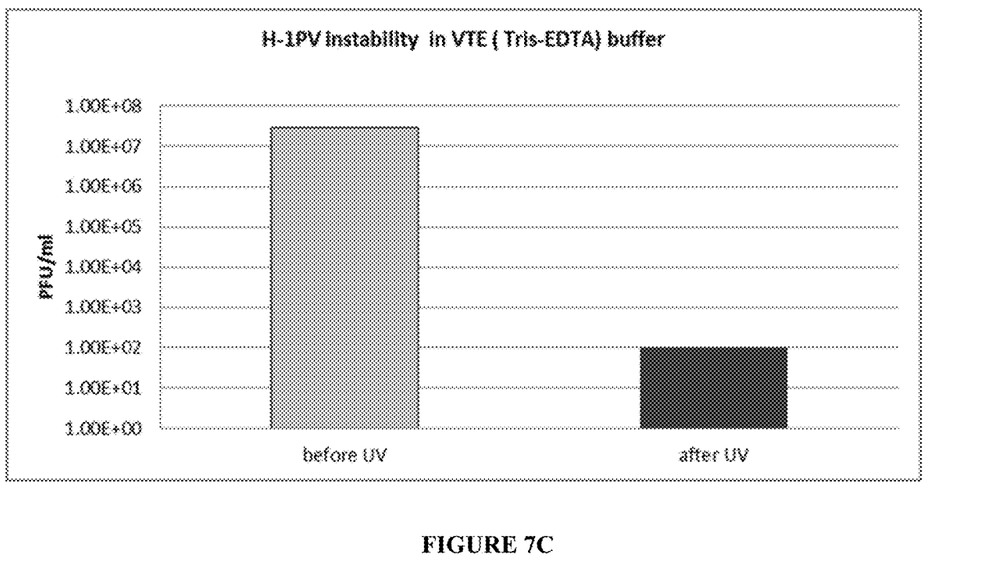

As can be concluded from FIGS. 6 and 7, the virus in 48% Iodixanol/Ringer solution remains active several days even after an temperature increase and an UV radiation.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1 VISIPAQUE™ (Iodixanol) 48% Avoids Backflow

A clinical phase I/IIa trial on 18 patients suffering from recurrent malignant gliomas was initiated. This trial aims to investigate the safety, biodistribution, maximum tolerated dose and signs of anti-tumor activity of parvovirus H-1. According to preclinical data the parvovirus will not only include intratumoral virus application but also intravenous treatment.

Figure 4:
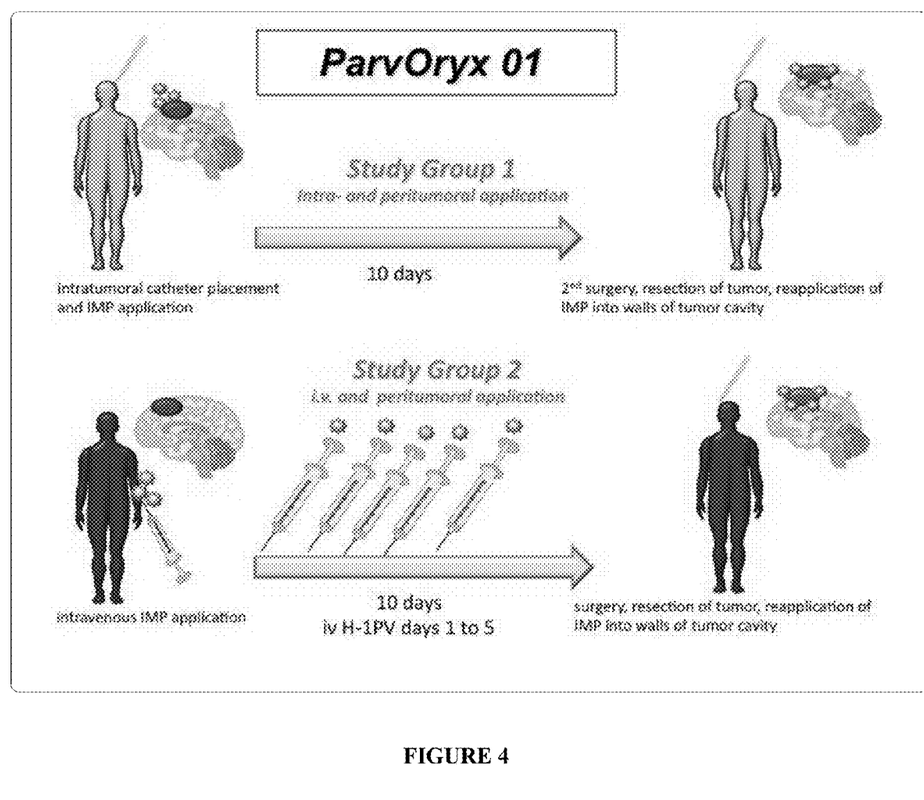
FIG. 4: Clinical Trial Design.

The application of parvovirus H-1 (GMP-grade preparation) in 48% VISIPAQUE™ (iodixanol) was performed in 2 groups of 12 (group I) and 6 patients (group II). The route of administration differs between group 1 and group 2 (FIG. 4).

Within each group the mode of application is identical, but the dose will be increased if no dose limiting events are observed. In group I the parvovirus H-1 (also called "investigational medicinal product"; IMP) was administered in four dose levels and in group II in 2 dose levels (Table 1).

TABLE 1

Dose schedule for both study groups

| Study Time | Dose and route of administration | Duration |
|---|---|---|
| GROUP I Escalation Level | | |
| Level 1 Total dose: $1 \times 10^6$ pfu | Day 1 — $5 \times 10^5$ pfu, intratumoral (via catheter) | 15 minutes |
| | Day 10 — $5 \times 10^5$ pfu, intracerebal (direct injection at multiple locations of resection wall) | 15-30 minutes |
| Level 2 Total dose: $5 \times 10^7$ pfu | Day 1 — $2.5 \times 10^7$ pfu, intratumoral (via catheter) | 15 minutes |
| | Day 10 — $2.5 \times 10^7$ pfu, intracerebal (direct injection at multiple locations of resection wall) | 15-30 minutes |
| Level 3 Total dose: $1 \times 10^9$ pfu | Day 1 — $5 \times 10^8$ pfu, intratumoral (via catheter) | 15 minutes |
| | Day 10 — $5 \times 10^8$ pfu, intracerebal (direct injection at multiple locations of resection wall) | 15-30 minutes |
| Level 4 Total dose: $5 \times 10^9$ pfu | Day 1 — $2.5 \times 10^9$ pfu, intratumoral (via catheter) | 15 minutes |
| | Day 10 — $2.5 \times 10^9$ pfu, intracerebal (direct injection at multiple locations of resection wall) | 15-30 minutes |
| GROUP II Escalation Level | | |
| Level 2 Total dose: $5 \times 10^7$ | Day 1-5 — $0.5 \times 10^7$ pfu, intravenous infusion | 2 hours |
| | Day 10 — $2.5 \times 10^7$ pfu, intracerebral (direct injection at multiple locations of resection wall) | 15-30 minutes |
| Level 3 Total dose: $1 \times 10^9$ pfu | Day 1-5 — $1 \times 10^8$ pfu, intravenous infusion | 2 hours |
| | Day 10 — $5 \times 10^8$ pfu, intracerebral (direct injection at multiple locations of resection wall) | 15-30 minutes |

In group 1 the patients received the IMP on day 1 via image guided injection into the tumor tissue. On this day the patient is injected with 50% of the intended overall dose.

After an observation period of 9 days the tumor was resected on day 10. After tumor removal the second half of the dose was administered into the walls of the resection cavity by direct injection. With this injection during open surgery the administration of the IMP is completed and no additional virus application was performed.

In group 2 the initial administration of the IMP was via the intravenous route. Subjects received 50% of the intended dose by 5 infusions on days 1 to 5, each infusion containing 10% of the total dose. After the last infusion on day 5 there is an observation period until day 9 and on day 10 tumor resection was performed as in group 1. In analogy to group 1, patients receive the second half of the dose by injection in the tissue surrounding the tumor cavity after tumor removal and no further virus injections were performed in each individual during the course of the trial.

After tumor resection virus was reapplied in the walls of the tumor cavity.

Figure 1:
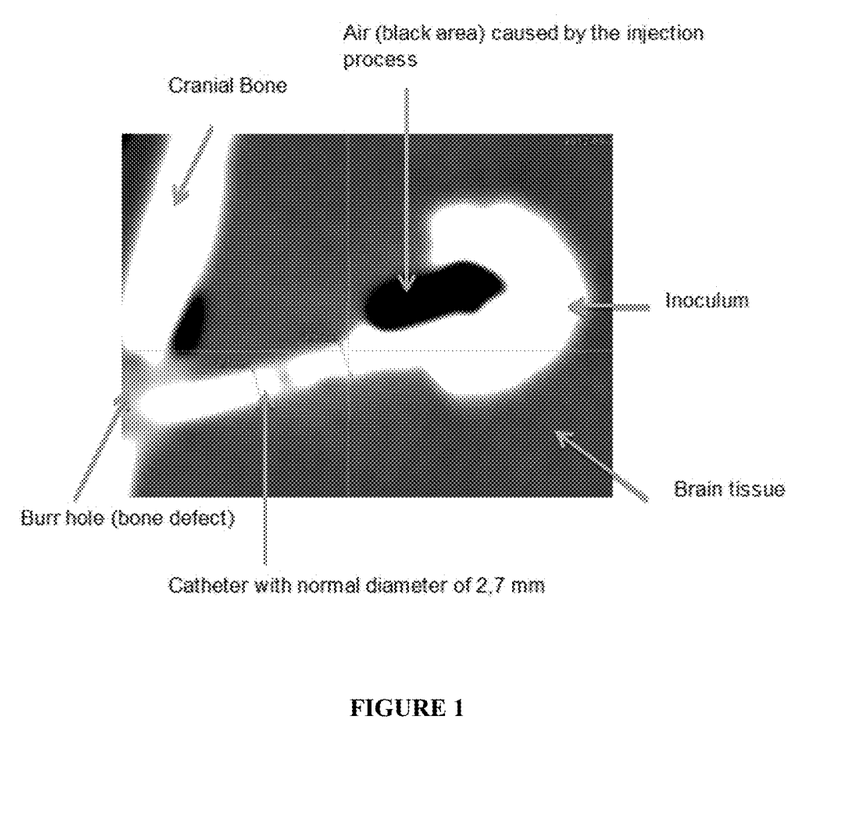
FIG. 1: H-1PV in 48% VISIPAQUE™ (iodixanol)/Ringer solution demonstrates the targeted distribution of the inoculum around the tip of the catheter without signs of random diffusion.
Figure 2:
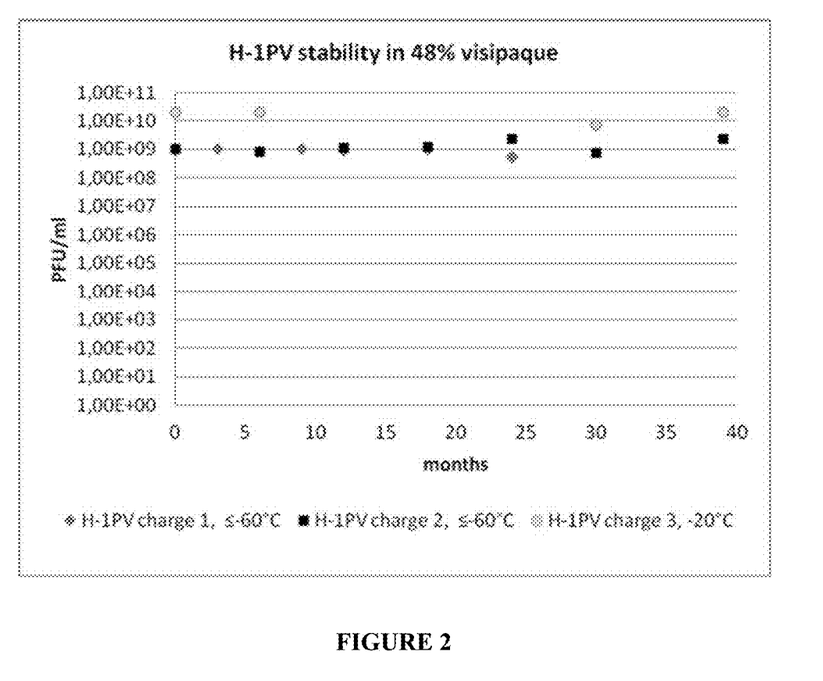
FIG. 2: H-1PV is stable for more than 24 months in 48% VISIPAQUE™ (iodixanol)/ringer formulation.
Figures 3A, 3B:
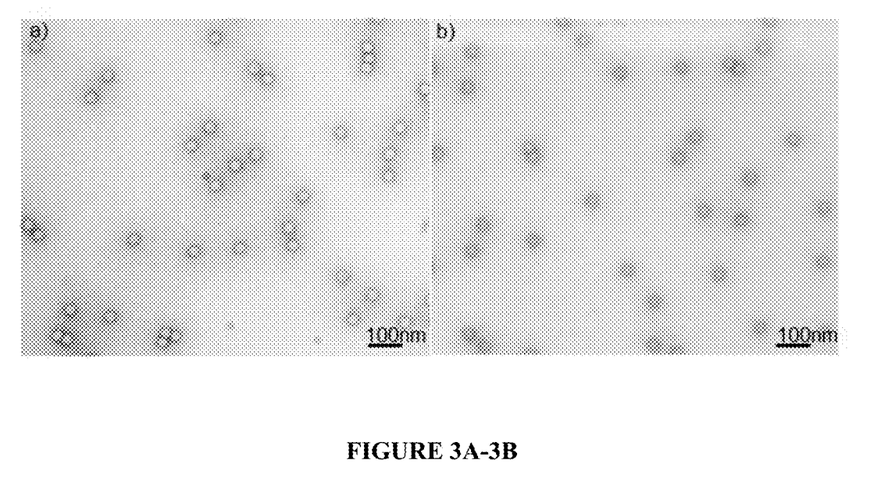
FIG. 3A-3B: Electron micrographs showing insular H-1PV particles in 48% VISIPAQUE™ (iodixanol)/ringer formulation a) H-1PV charge 1, b) H-1PV charge 2.

As shown in FIG. 1 the use of VISIPAQUE™ (iodixanol) 48% (VISIPAQUE™ 320, GE Healthcare, Germany) and Ringer solution (IDT Biologika GmbH, Germany) as carrier solution did not result in any significant backflow in all 12 patients. The CT was performed within 30 minutes after completion of injection. The volume of injection was between 0.5 ml to 1.2 ml per inserted catheter (3 patients were treated with 2 catheters). The injection was performed manually over a period of 30 min per catheter and standard catheters for cyst puncturing with one opening at the end of the catheter were used in all cases. FIG. 1 also demonstrates the targeted distribution of the inoculum around the tip of the catheter without signs of random diffusion.

From this clinical data it can be concluded that the use of VISIPAQUE™ (iodixanol) 48% allows for (i) precise visualization of the inoculum by CT, (ii) precise local delivery as a result of the higher viscosity and (iii) the absence of backflow even when manual injection and no prolonged and automated injection such as convection enhanced delivery (CED) was used. This favorable pattern of distribution is most likely due to the different physical properties of VISIPAQUE™ (iodixanol) 48% compared with watery solutions. VISIPAQUE™ (iodixanol) 48% in Ringer solution with a refraction index of 1.41 has a viscosity at 37° C. of 4 mPa·s, water at 37° C. of ~0.7 mPa·s. The human blood at 37° C. has a viscosity of ~4.5 mPa·s. Therefore the injection formulation is close to blood, that means in a physiological value of blood.

Example 2 Stability

The H-1PV virus (stored by −20° C. or ≤−60° C. in 48% Iodixanol/Ringer solution obtained by mixing 73.62% (w/v) VISIPAQUE™ (iodixanol) 320 (GE Healthcare) with 26.30% (w/v) Ringer solution (Delta Select GmbH, Dreieich, Germany)) is stable in activity measured with plaque forming units (PFU) for more than 2 years. Plaque assays were done essentially as described by Tattersall and Bratton (J. Virol. 46 (1983), 944-55). NB-324K cells were grown in monolayer cultures in MEM medium containing 5% FBS, 100 µg/ml penicillin, 100 µg/ml streptomycin, and 2 mM L-glutamine. They were infected at 60% confluence with serial dilutions of H-1PV and incubated for 1 h at 37° C. Then the inoculum was replaced with a bacto-agar overlay (1.7% in MEM containing 5% FBS). On day four post-infection, living cells were stained for 18-24 h by addition of 0.02% toluylene red staining solution (Sigma, Germany) containing bacto-agar (Becton Dickinson, Germany). The dishes were incubated at 37° C. under 5% $CO_2$. Plaque-forming units were counted 5 days post-infection on a light box and their concentration expressed in PFU/ml.

The results are shown in FIG. 5. There it can be seen that a virus concentration less than $1 \times 10^8$ pfu/ml is more instable in 48% Iodixanol/Ringer solution than a higher virus concentration of about $1 \times 10^9$ or $1 \times 10^{10}$ pfu/ml.

Example 3 Insular H-1PV Particles: The Electron Microscopy Pictures Show that the H-1PV Virus is not Aggregated in the Formulation According to the Invention For qualitative analysis of virus preparations, electron microscopy pictures were taken. For this, 5 µl virus suspension was added to a ready-to-use carbon-coated copper grid and incubated for 2 min. The grid was then washed with 5 µl bidest water and coated with 2% uranyl acetate for 30 s. The drops were absorbed from the grid with Whatman 50 filter paper and the grid was dried for approximately 1 min. Photos were taken with a Zeiss transmission electron microscope at 20,100× magnification.

Example 4 Influence of Temperature Increase to H-1PV in 48% VISIPAQUE™ (Iodixanol)/Ringer Solution Parameter:
Volume: 100 µl
Vial: 500 µl screw cap
Temperatur: 37° C., 50° C.
Incubation time: 1 h, 4 h
Further storage: 4° C.
Concentration H-1PV: $2.3 \times 10^{10}$ PFU/ml:

|  |  | Time 1 | Time 2 |
|---|---|---|---|
| Temp. | 37° C. | 60 min | 240 min |
|  | 50° C. | 60 min | 240 min |

The results are shown in FIG. 6.

FIG. 6 shows that the virus is still alive after 1-4 hours at 37° C. and 50° C. treatment. Even after 4 weeks in 4° C. the H-1 PV is stable.

Example 5 Influence of UV Radiation to H-1PV in 48% VISIPAQUE™ (Iodixanol)/Ringer Solution UV-Deactivation of H-1PV in VISIPAQUE™ (iodixanol) (48% Iodixanol)/Ringer solution and VISIPAQUE™ (iodixanol) (24% Iodixanol)/Ringer solution

| exp# 1 (UV 254 nm, 0.35 mW/cm²) | | | | |
|---|---|---|---|---|
|  |  | PFU/ml | Vg/ml | PP/ml |
| Charge 1 in VISIPAQUE ™ (iodixanol) (48% Iod)/Ringer volume: 500 µl | before UV | 1.80E+09 | 1.40E+12 | 1.00E+13 |
|  | after UV | 2.00E+09 | 1.30E+12 | 8.00E+12 |
| Charge 2 in VISIPAQUE ™ (iodixanol) (48% Iod)/Ringer volume: 500 µl | before UV | 1.30E+08 | 7.30E+10 | 2.00E+11 |
|  | after UV | 6.40E+07 | 8.10E+10 | 2.10E+11 |

| exp# 2 (UV 254 nm, 0.35 mW/cm²) | | | | |
|---|---|---|---|---|
| | | PFU/ml | Vg/ml | PP/ml |
| Charge 1 in VISIPAQUE ™ (iodixanol) (48% Iod)/Ringer volume: 250 µl | before UV | 1.80E+09 | 1.40E+12 | 1.00E+13 |
| | after UV | >3E7 | 1.40E+12 | 1.00E+13 |
| Charge 2 in VISIPAQUE ™ (iodixanol) (48% Iod)/Ringer volume: 250 µl | before UV | 1.30E+08 | 7.30E+10 | 2.00E+11 |
| | after UV | >3E7 | 7.30E+10 | 3.10E+11 |
| Charge 3 in VTE | before UV | 3.00E+07 | 5.40E+11 | 4.10E+13 |
| | after UV | <1E2 | 2.80E+10 | 5.60E+13 |

| exp# 3 (UV 254 nm, 0.35 mW/cm²) | | | | |
|---|---|---|---|---|
| | | PFU/ml | Vg/ml | PP/ml |
| Charge 1 in VISIPAQUE ™ (iodixanol) (48% Iod)/Ringer volume: 100 µl | before UV | 1.40E+09 | 9.50E+11 | 1.00E+13 |
| | after UV | 2.40E+09 | 1.00E+12 | 1.10E+13 |
| Charge 2 in VISIPAQUE ™ (iodixanol) (48% Iod)/Ringer volume: 100 µl | before UV | 5.10E+07 | 5.00E+10 | 2.00E+11 |
| | after UV | 5.80E+07 | 5.00E+10 | 2.00E+11 |

| exp# 4 (UV 254 nm, 2.4 mW/cm²) | | | | |
|---|---|---|---|---|
| | | PFU/ml | Vg/ml | PP/ml |
| Charge 1 in VISIPAQUE ™ (iodixanol) (48% Iod)/Ringer volume: 100 µl | before UV | 1.70E+09 | 1.40E+12 | 9.80E+12 |
| | after UV | 1.80E+09 | 1.70E+12 | 7.70E+12 |
| Charge 2 in VISIPAQUE ™ (iodixanol) (24% Iod)/Ringer volume: 100 µl | before UV | 4.60E+09 | 6.80E+11 | 1.00E+13 |
| | after UV | 1.20E+09 | 4.10E+11 | 3.50E+11 |

The results are shown in FIG. 7. The H-1 PV virus in VISIPAQUE™ (iodixanol) (48% Iodixanol)/Ringer solution is protected against UV treatment through the formulation. The stability of the virus in VISIPAQUE™ (iodixanol) (24% Iodixanol)/Ringer solution shows a half log decrease after UV treatment. In an aqueous formulation (Tris-EDTA buffer=VTE) the virus could be deactivated.

The invention is further described by the following numbered paragraphs:

1. A pharmaceutical composition comprising (a) at least $2\times10^9$ pfu/ml of parvovirus H1 (H-1PV) or a related rodent parvovirus selected from the group consisting of LuIII, Mouse minute virus (MMV), Mouse parvovirus (MPV), Rat minute virus (RMV), Rat parvovirus or Rat virus (RV) and (b) a pharmaceutically acceptable carrier containing 40-50% Iodixanol (w/v), 0.7-0.9 mmol CaCl$_2$×2 H$_2$O, 50-60 mmol NaCl, 0.9-1.2 mmol KCl, 0.7-0.95 mg/ml Tromethamine and 0.05-0.15 mg/ml Edetate calcium disodium.

2. The pharmaceutical composition of paragraph 1, wherein the pharmaceutical acceptable carrier contains 48% Iodixanol (w/v), 0.81 mmol CaCl$_2$×2 H$_2$O, 52.80 mmol NaCl, 1.06 mmol KCl, 0.88 mg/ml Tromethamine and 0.07 mg/ml Edetate calcium disodium.

3. The pharmaceutical composition of paragraph 1 or 2, wherein the parvovirus concentration is between $2\times10^9$ pfu/ml and $1\times10^{10}$ pfu/ml.

4. The pharmaceutical composition of any one of paragraphs 1 to 3 for use in treating a tumor by intratumoral or intravenous injection.

5. The pharmaceutical composition of any one of paragraphs 1 to 3 for the use according to claim 4, wherein the tumor is a brain tumor, pancreatic carcinoma, cervical carcinoma, lung cancer, head and neck cancer, breast cancer or colon cancer.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for treating a tumor comprising intratumoral or intravenous injection of a pharmaceutical composition comprising (a) at least $2\times10^9$ pfu/ml of parvovirus H1 (H-1PV) or a related rodent parvovirus selected from the group consisting of LuIII, Mouse minute virus (MMV), Mouse parvovirus (MPV), Rat minute virus (RMV), Rat parvovirus and Rat virus (RV) and (b) a pharmaceutically acceptable carrier containing 40-50% Iodixanol (w/v), 0.7-0.9 mmol CaCl$_2$×2 H$_2$O, 50-60 mmol NaCl, 0.9-1.2 mmol KCl, 0.7-0.95 mg/ml Tromethamine and 0.05-0.15 mg/ml Edetate calcium disodium, wherein the viscosity of the carrier is between 3.5 to 4.5 mPa·s at 37 to 40° C.

2. The method according to claim 1, wherein the tumor is a brain tumor, pancreatic carcinoma, cervical carcinoma, lung cancer, head and neck cancer, breast cancer or colon cancer.

3. The method of claim 1, wherein the pharmaceutical acceptable carrier contains 48% Iodixanol (w/v), 0.81 mmol CaCl$_2$×2 H$_2$O, 52.80 mmol NaCl, 1.06 mmol KCl, 0.88 mg/ml Tromethamine and 0.07 mg/ml Edetate calcium disodium.

4. The method according to claim 3, wherein the tumor is a brain tumor, pancreatic carcinoma, cervical carcinoma, lung cancer, head and neck cancer, breast cancer or colon cancer.

5. The method of claim 1, wherein the parvovirus concentration is between $2\times10^9$ pfu/ml and $1\times10^{10}$ pfu/ml.

6. The method according to claim 5, wherein the tumor is a brain tumor, pancreatic carcinoma, cervical carcinoma, lung cancer, head and neck cancer, breast cancer or colon cancer.

7. The method of claim 3, wherein the parvovirus concentration is between $2\times10^9$ pfu/ml and $1\times10^{10}$ pfu/ml.

8. The method according to claim 7, wherein the tumor is a brain tumor, pancreatic carcinoma, cervical carcinoma, lung cancer, head and neck cancer, breast cancer or colon cancer.

9. A method for treating a tumor comprising intratumoral or intravenous injection of a pharmaceutical composition comprising (a) at least $2\times10^9$ pfu/ml of parvovirus H1 (H-1PV) or a related rodent parvovirus selected from the group consisting of LuIII, Mouse minute virus (MMV), Mouse parvovirus (MPV), Rat minute virus (RMV), Rat parvovirus and Rat virus (RV) and
(b) a pharmaceutically acceptable carrier containing 40-50% Iodixanol (w/v), 0.7-0.9 mmol $CaCl_2 \times 2\ H_2O$, 50-60 mmol NaCl, 0.9-1.2 mmol KCl, 0.7-0.95 mg/ml Tromethamine and 0.05-0.15 mg/ml Edetate calcium disodium,
wherein the viscosity of the carrier is between 4 and 5 mPa·s.

10. The method according to claim 9, wherein the tumor is a brain tumor, pancreatic carcinoma, cervical carcinoma, lung cancer, head and neck cancer, breast cancer or colon cancer.

11. The method of claim 9, wherein the pharmaceutical acceptable carrier contains 48% Iodixanol (w/v), 0.81 mmol $CaCl_2 \times 2\ H_2O$, 52.80 mmol NaCl, 1.06 mmol KCl, 0.88 mg/ml Tromethamine and 0.07 mg/ml Edetate calcium disodium.

12. The method according to claim 11, wherein the tumor is a brain tumor, pancreatic carcinoma, cervical carcinoma, lung cancer, head and neck cancer, breast cancer or colon cancer.

13. The method of claim 9, wherein the parvovirus concentration is between $2\times10^9$ pfu/ml and $1\times10^{10}$ pfu/ml.

14. The method according to claim 13, wherein the tumor is a brain tumor, pancreatic carcinoma, cervical carcinoma, lung cancer, head and neck cancer, breast cancer or colon cancer.

15. The method of claim 11, wherein the parvovirus concentration is between $2\times10^9$ pfu/ml and $1\times10^{10}$ pfu/ml.

16. The method according to claim 15, wherein the tumor is a brain tumor, pancreatic carcinoma, cervical carcinoma, lung cancer, head and neck cancer, breast cancer or colon cancer.

17. The method of claim 9, wherein the viscosity of the carrier is about 4.5 mPa·s.

* * * * *